United States Patent [19]

Bithell

[11] 4,321,232
[45] Mar. 23, 1982

[54] PACKAGE AND STERILIZING PROCESS FOR SAME

[75] Inventor: Roger M. Bithell, Richmond, Calif.

[73] Assignee: Tegal Corporation, Novato, Calif.

[21] Appl. No.: 134,015

[22] Filed: Mar. 25, 1980

[51] Int. Cl.³ .............................................. A61L 2/14
[52] U.S. Cl. ..................................... 422/23; 250/455; 422/21; 422/22
[58] Field of Search ...................... 250/453, 455, 531; 422/21, 22, 23

[56] References Cited

U.S. PATENT DOCUMENTS

| | | |
|---|---|---|
| 3,076,373 | 4/1975 | Glyptis .............................. 422/22 X |
| 3,851,436 | 12/1974 | Fraser et al. ...................... 422/22 X |
| 3,948,601 | 4/1976 | Fraser et al. ...................... 422/23 |
| 3,955,921 | 5/1976 | Tensmeyer ......................... 422/22 |
| 4,042,325 | 8/1977 | Tensmeyer ......................... 422/22 |
| 4,207,286 | 6/1980 | Gutboucher ........................ 422/21 |

*Primary Examiner*—Barry Richman
*Attorney, Agent, or Firm*—Paul F. Wille

[57] ABSTRACT

A sterilizable package in which a porous envelope containing the article to be sterilized is subjected to a plasma, said plasma being generated outside of said envelope with the reactive components of the plasma passing through said porous envelope, thereby sterilizing the article through the package.

4 Claims, 4 Drawing Figures

PACKAGE AND STERILIZING PROCESS FOR SAME

BACKGROUND OF THE INVENTION

This invention relates to a package for use in plasma sterilizing equipment and to a process for sterilizing articles in a package or container.

In the prior art, a host of processes have been proposed and/or used for sterilizing, such as heat, either wet or dry; chemicals; beta, gamma, or ultraviolet radiation; electron beams; microwaves; arc discharges; lasers; and plasma. In the particular case of sterilizing an article or substance inside a container, package, or other enclosure, chemicals and lasers have been used or proposed.

Problems with prior art techniques for sterilizing into or through an enclosure are lack of operating ease and dangerous or toxic conditions or substances. Use of these techniques has generally been restricted to large industrial concerns which have and can afford adequate safety equipment. A particular problem with the use of chemicals, e.g. ethylene oxide, is the length of time required to process a single batch, about twenty four hours. Thus the process is only viable on a large scale. A particular problem with lasers is the control, focussing and manipulation of same to assure complete sterilization.

Using a plasma to sterilize articles in a package is disclosed in U.S. Pat. Nos. 3,851,436 and 3,948,601. However, the system therein described does not sterilize through a package but pumps a plasma through a plastic bag containing the article to be sterilized and later seals the bag to maintain sterility. While suitable for use in specialized applications, the process and apparatus described are unsuitable for general use in medical applications due to the article being remote from the plasma generator, the need to pump the plasma (more likely the ions or free radicals resulting therefrom) through the article, and the need to later seal under sterile conditions.

In view of the foregoing, it is therefore an object of the present invention to provide a simplified process for sterilizing articles in a package.

A further object of the present invention is to provide a package for use in a sterilizing plasma.

Another object of the present invention is to provide a process for sterilizing articles through a package by the use of a plasma.

SUMMARY OF THE INVENTION

The foregoing objects are achieved through the present invention wherein it has been found that sealed packages can be placed in a plasma and the article contained therein sterilized through the package. Further, the article remains sterile until the package is opened. For flat packages, e.g. containing hypodermic needles, the major surfaces, herein referred to as "front" and "back", are preferably both plastic. Alternatively, a surface may comprise paper, with consequent increase in processing time for outgassing the paper.

Prior to a detailed description of the present invention, some terminology should be defined. As unlikely as it may seem, despite the century or so since the work of Pasteur and his contemporaries, "sterile" does not appear to have a clear medical definition. Some consider sterile to mean no living thing, i.e. barren. Some consider sterile to mean incapable of reproduction, i.e. inert. Some consider sterile to mean no harmful microorganisms, i.e. benign. A few consider sterile to mean no foreign matter at all, i.e. clean.

While one could use a circular definition, e.g. that which is accepted by the medical profession as sterile, such is not entirely helpful. Of late, there appears to be developing a result oriented, probabilistic approach to defining sterility, e.g. "Guide to sterility assurance for medical devices", 79-EHD-32, Ministry of National Health and Welfare, Canada, April, 1979. This approach defines process and test procedures by which one attains sterility in the sense of either benign or inert; sterility in the sense of barren being considered difficult to prove. Under this approach, sterile means being subjected to a process whereby the probability of a surviving contaminant is very low. This is the meaning intended here.

Another term which has been used somewhat loosely in this area is "plasma". As used herein, a plasma is an essentially neutral cloud of ions and/or free radicals in which atoms or molecules are ionized, dissociated, or excited by an applied field, often a radio frequency (RF) field. A plasma is not an arc discharge. In a plasma, the gas or gas mixture is usually at a relatively low pressure, e.g. 100 Torr (13 kPa) or lower, at a relatively low temperature, ambient to 80° C. or so and the plasma is induced at relatively low energy density, e.g. 0.5 $W/cm^2$ or less. In an arc discharge, the pressure is generally ambient or higher, the temperature of the arc is extremely high, 1000° C. or higher, and the energy density is high. "Energy density" is the applied power divided by the area occupied by an electrode, or the smaller electrode if the electrodes are not the same size.

Finally, as used herein, "porous" means that a closed package not having holes visible to the unaided eye is able to withstand, without rupture, a pump down within 60–90 seconds from 101 kPa (atmospheric) to 6.7 kPa (50 Torr) pressure and is penetrated by the active plasma species during sterilization.

BRIEF DESCRIPTION OF THE DRAWINGS

A more complete understanding of the present invention can be obtained by considering the following detailed description in conjunction with the accompanying drawings in which.

DETAILED DESCRIPTION

Figure 1:
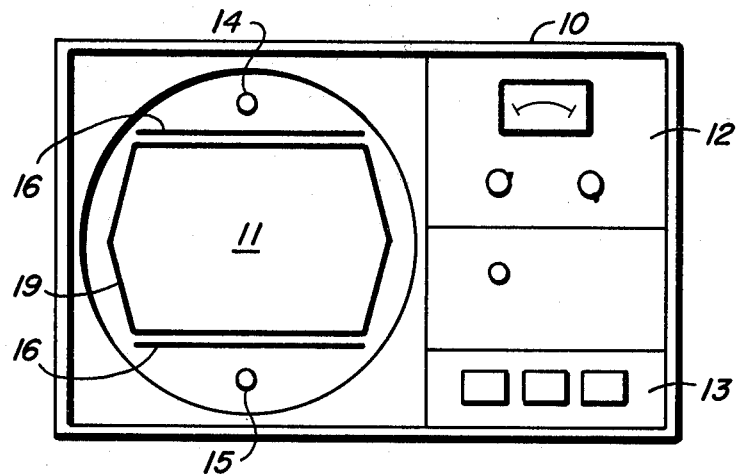
FIG. 1 illustrates a plasma reactor for use in the present invention.

As illustrated in FIG. 1, plasma reactor 10 comprises chamber 11 of any suitable shape, process monitoring equipment 12, and process control equipment 13. In the particular embodiment illustrated in FIG. 1, chamber 11 comprises a cylindrical section made from any suitable material such as aluminum or quartz. Interior to chamber 11 are gas supply port 14 and exhaust port 15, respectively. Within chamber 11, the plasma is induced between and adjacent to RF electrodes 16. Between electrodes 16 are one or more or more shelves 19 for supporting the packages to be sterilized.

Figure 4:
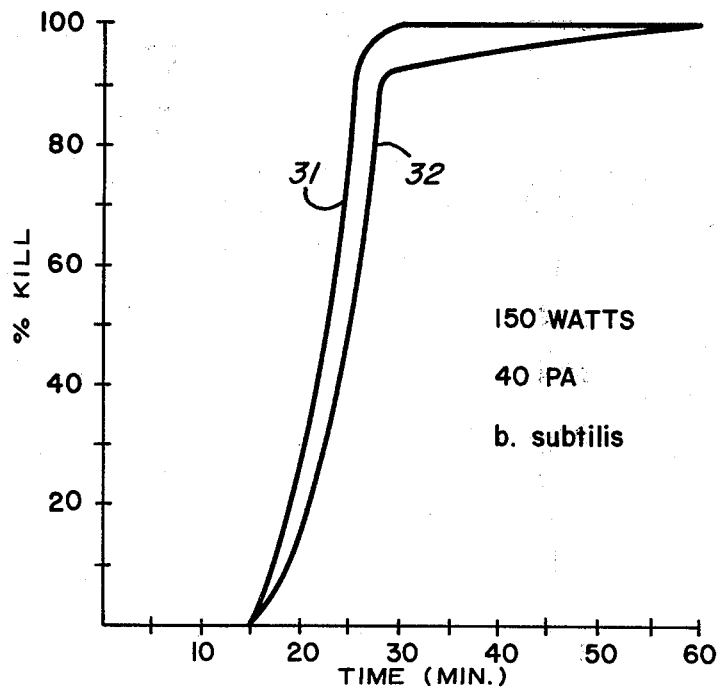
FIG. 4 illustrates the effect on processing time of stacking packages.

To assure a short sterilization time, it is preferred that the packages not be stacked too densely on a shelf, e.g. not more than five deep, since the interior packages tend to be shielded by those on the outside. As illustrated in FIG. 4, the processing time increases with stacking, if all other conditions are unchanged. Specifically, curve 31 corresponds to a single layer of packages, while curve 32 corresponds to stacked packages. As is apparent to those of skill in the art, the maximum number of packages that may be stacked one on the other is readily determined empirically and depends upon the nature and size of package. For relatively flat packages containing dressings or hypodermic needles, several shelves may be utilized to assure that the packages are not stacked more than about five deep.

Figure 2:
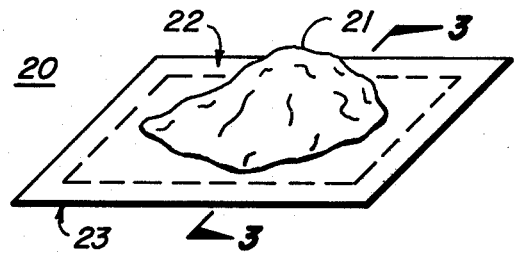
FIG. 2 illustrates a package in accordance with the present invention.

FIG. 2 illustrates a typical, relatively flat package suitable for use in the present invention. In particular, package 20 comprises a front and back major surface comprising a porous material. Suitable materials include "green tubing", polyethylene, as sold by American Hospital Supply Corporation. Packages suitable for use in the present invention are also made by Edward Weck & Company under the tradename "Weck Peel/Pack"; Minnesota Mining and Manufacturing Company, under the tradename "Steri-Lock"; and Tower Products under the tradename "Dual Peel".

While preferably comprising plastic front and back surfaces, either of the surfaces may comprise paper with the attendant increase in processing time for outgassing of the paper. As illustrated in FIG. 2, the front and back surfaces are formed around article 21, which is to be kept sterile. The edges 22 of package 20 are then suitably sealed to fully enclose the article. Package 20 is then inserted into plasma reactor 10 and subjected to a gas plasma for a suitable period of time to sterilize the article within. While a variety of gases are suitable, it has for example been found that an oxygen plasma at a pressure of 40 Pa (0.3 torr) for sixty minutes with an applied power of 150 watts will sterilize articles through the package. After the sterilization period is completed, the articles are removed from the reactor and may be stored or sent to the user. While it is an advantage of the present invention that the package may be conveniently fully sealed prior to sterilization, it is understood that one could seal, for example, only three sides of the package prior to sterilization and seal the fourth side subsequent to the plasma sterilization process.

Figure 3:
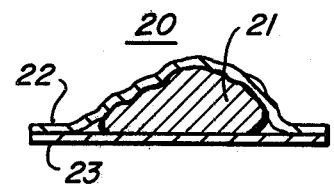
FIG. 3 illustrates in cross-section a package in accordance with the present invention.

FIG. 3 illustrates in cross-section a package in accordance with the present invention wherein article 21 is enclosed by front and back surfaces 22 and 23 respectively having the edges thereof sealed. While illustrated in FIG. 3 as comprising a simple contact seal, it is understood that any suitable sealing mechanism may be used. For example, the two layers of plastic may be folded over to form a heavier edge, thereby preventing accidential opening of the package. Further, while illustrated as two separate pieces 22 and 23, it is understood that one may simply fold a single piece of material to obtain the desired package.

There is thus provided by the present invention an improved sterilization and packaging system wherein the packages can be fully closed and sealed prior to the sterilization process. The sterilization process itself is distinctly superior to prior art sterilization systems in that toxic byproducts or residues, as obtained in ethylene oxide sterilization, are not introduced by the present invention. since one can much more rapidly sterilize packaged articles, even a relatively small plasma reactor is capable of sterilizing a much larger quantity of articles than has heretofore been obtainable in the prior art.

Having thus described the invention, it will be apparent to those of skill in the art that various modifications can be made within the spirit and scope of the present invention. For example, the particular gas chosen, pressure, final temperature, and number of packages, are parameters to be decided by the user depending upon the particular article being sterilized.

I claim:

1. A process for sterilizing an article enclosed in a porous container comprising the steps of:
   placing a porous container having an article enclosed therein in a plasma reactor;
   inducing a plasma within said reactor such that the exterior of said container is exposed to reactive components of said plasma; and
   maintaining said plasma within said reactor and outside of said container for a sufficient length of time for said reactive components to act through said porous container to an extent such that the probability of a microbiological contaminant surviving on said article located therein is very low.

2. The process as set forth in claim 1 wherein a plurality of said articles are sterilized simultaneously in said plasma reactor.

3. The process as set forth in claim 2 wherein said articles are each enclosed in a porous container and said plasma surrounds the plurality of containers.

4. The process as set forth in claim 3 wherein said articles have flat surfaces and further comprising the step of:
   stacking said articles no more than five deep in said plasma reactor.

* * * * *

REEXAMINATION CERTIFICATE (3391th)

United States Patent [19]
Bithell

[11] B1 4,321,232
[45] Certificate Issued Dec. 9, 1997

[54] PACKAGE AND STERILIZING PROCESS FOR SAME

[75] Inventor: Roger M. Bithell, Richmond, Calif.

[73] Assignee: Abtox Inc, Mundelein, Ill.

Reexamination Request:
No. 90/004,642, May 16, 1997

Reexamination Certificate for:
Patent No.: 4,321,232
Issued: Mar. 23, 1982
Appl. No.: 134,015
Filed: Mar. 25, 1980

[51] Int. Cl.$^6$ .................................................. A61L 2/14
[52] U.S. Cl. ...................... 422/23; 250/455.11; 422/21; 422/22
[58] Field of Search ......................... 422/23, 21, 22; 250/455.11

[56] References Cited

U.S. PATENT DOCUMENTS

| | | | |
|---|---|---|---|
| 3,490,580 | 1/1970 | Brumfield et al. | |
| 3,551,090 | 12/1970 | Brumfield et al. | |
| 3,851,436 | 12/1974 | Fraser et al. | 422/22 X |
| 3,876,373 | 4/1975 | Glyptis | 422/22 X |
| 3,948,601 | 4/1976 | Fraser et al. | 422/23 |
| 3,955,921 | 5/1976 | Tensmeyer | 422/22 |
| 4,042,325 | 8/1977 | Tensmeyer | 422/22 |
| 4,207,286 | 6/1980 | Gutboucher | 422/21 |

FOREIGN PATENT DOCUMENTS

| | | |
|---|---|---|
| 873482 | 6/1971 | Canada. |
| 1231316 | 5/1971 | United Kingdom. |

OTHER PUBLICATIONS

ASP's Motion & Memorandum in Support of Motion for SJ.
ASP's Summary of Argument and Evidence in Support . . . .
Declaration of Henrik D. Parker . . . .
Abtox's Opposition to JJMI's Motion for Summ. Adjudication.
Declaration of Kenenth B. Stalder . . . .
Declaration of James P. McVittie . . . .
Declaration of Daniel R. Hansen . . . .
Declaration of Ross A. Caputo . . . .
ASP's Reply Memorandum in Support of Motion for Summ. Adjud.
Reply Declaration of Henrik D. Parker . . . .
Reply Declaration of Richard B. Timmons . . . .
Declaration of Richard B. Timmons . . . .
Declaration of John R. Gillis . . . .

*Primary Examiner*—Krisanne M. Thornton

[57] ABSTRACT

A sterilizable package in which a porous envelope containing the article to be sterilized is subjected to a plasma, said plasma being generated outside of said envelope with the reactive components of the plasma passing through said porous envelope, thereby sterilizing the article through the package.

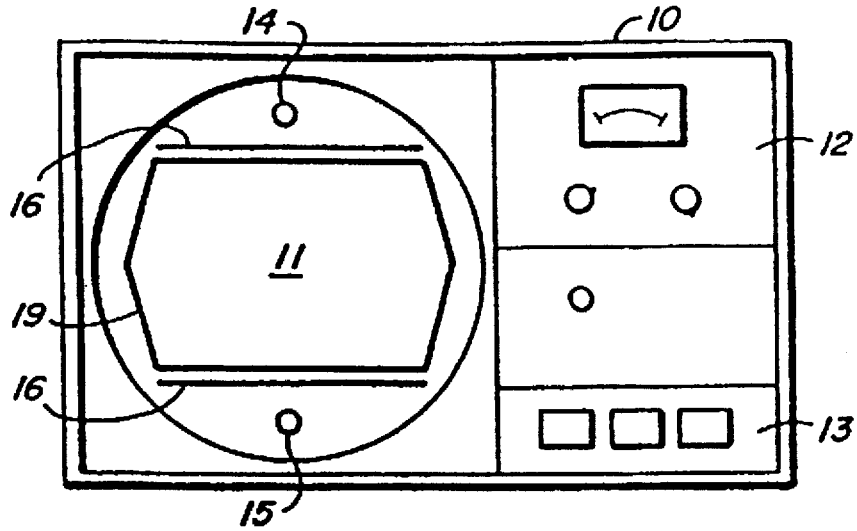

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-4 is confirmed.

* * * * *